United States Patent

Hooven

[11] Patent Number: 6,086,586
[45] Date of Patent: Jul. 11, 2000

[54] BIPOLAR TISSUE GRASPING APPARATUS AND TISSUE WELDING METHOD

[75] Inventor: Michael D. Hooven, Cincinnati, Ohio

[73] Assignee: Enable Medical Corporation, West Chester, Ohio

[21] Appl. No.: 09/152,397

[22] Filed: Sep. 14, 1998

[51] Int. Cl.⁷ .................................................. A61B 18/18
[52] U.S. Cl. ................................ 606/50; 606/48; 606/51
[58] Field of Search ................................ 600/48, 50, 51, 600/11

[56] References Cited

U.S. PATENT DOCUMENTS

| | | |
|---|---|---|
| 1,496,438 | 6/1924 | Wallerich . |
| 1,852,542 | 4/1932 | Sovatkin . |
| 1,881,250 | 10/1932 | Tomlinson . |
| 1,918,889 | 7/1933 | Bacon . |
| 2,002,594 | 5/1935 | Wrappler et al. . |
| 2,031,682 | 2/1936 | Wrappler et al. . |
| 3,100,489 | 8/1963 | Bagley . |
| 3,270,745 | 9/1966 | Wood . |
| 3,775,825 | 12/1973 | Wood et al. . |
| 3,856,016 | 12/1974 | Davis . |
| 4,033,351 | 7/1977 | Hetzel . |
| 4,038,984 | 8/1977 | Sittner . |
| 4,041,952 | 8/1977 | Morrison, Jr. et al. . |
| 4,085,756 | 4/1978 | Weaver . |
| 4,114,623 | 9/1978 | Meinke et al. . |
| 4,128,099 | 12/1978 | Bauer . |
| 4,201,314 | 5/1980 | Samuels et al. . |
| 4,397,312 | 8/1983 | Molko . |
| 4,503,855 | 3/1985 | Maslanka . |
| 4,608,981 | 9/1986 | Rothfuss et al. . |
| 4,633,874 | 1/1987 | Chow et al. . |
| 4,646,751 | 3/1987 | Maslanka . |
| 4,655,216 | 4/1987 | Tischer . |
| 4,658,819 | 4/1987 | Harris et al. . |
| 4,671,274 | 6/1987 | Sorochenko . |
| 4,682,598 | 7/1987 | Beraha . |
| 4,682,606 | 7/1987 | DeCaprio . |
| 4,712,544 | 12/1987 | Ensslin . |

(List continued on next page.)

FOREIGN PATENT DOCUMENTS

| | | |
|---|---|---|
| 0 517 244 | 12/1992 | European Pat. Off. . |
| 0 518 230 | 12/1992 | European Pat. Off. . |
| 0 623 316 | 11/1994 | European Pat. Off. . |
| 0 717 967 | 6/1996 | European Pat. Off. . |
| 0 722 696 | 7/1996 | European Pat. Off. . |
| 0 724 863 | 8/1996 | European Pat. Off. . |
| 0 737 446 | 10/1996 | European Pat. Off. . |
| 0 737 447 | 10/1996 | European Pat. Off. . |
| 0 765 639 | 4/1997 | European Pat. Off. . |
| WO 85/00280 | 1/1985 | WIPO . |
| WO 93/08754 | 5/1993 | WIPO . |
| WO 93/13719 | 7/1993 | WIPO . |

OTHER PUBLICATIONS

Sugita, K. et al, "Bipolar coagulator with automatic thermocontrol," J. Neurosurg., vol. 41, pp. 777–779, Dec., 1974.
HHS Phase 1 Grant Application, "RF Bipolar Tissue Welding", dated Dec. 5, 1996 (portions redacted).

Primary Examiner—Linda C. M. Dvorak
Assistant Examiner—David M. Ruddy
Attorney, Agent, or Firm—Cook, Alex, McFarron, Manzo, Cummings & Mehler, Ltd.

[57] ABSTRACT

A bipolar electrosurgical instrument having a pair of relatively moveable jaws, each of which includes a tissue contacting surface. The tissue contacting surfaces of the jaws are in face-to-face relation with one another, and adjacent each of the tissue contacting surfaces are first and second spaced-apart electrodes that are adapted for connection to the opposite terminals of a bipolar RF generator so as to generator a current flow therebetween. The first and second electrodes of one jaw are in opposed relation, respectively, with the first and second electrodes of the other jaw. The tissue contacting surfaces are disposed between the electrodes on each jaw, and the first opposed electrodes of each jaw are connectable to one terminal of the bipolar RF generator, while the second opposed electrodes of each jaw are connectable to the other terminal of the bipolar RF generator.

29 Claims, 3 Drawing Sheets

U.S. PATENT DOCUMENTS

| | | |
|---|---|---|
| 4,712,549 | 12/1987 | Peters et al. . |
| 4,819,633 | 4/1989 | Bauer et al. . |
| 4,985,030 | 1/1991 | Melzer et al. . |
| 5,057,107 | 10/1991 | Parins et al. . |
| 5,085,659 | 2/1992 | Rydell . |
| 5,104,025 | 4/1992 | Main et al. . |
| 5,122,137 | 6/1992 | Lennox . |
| 5,147,357 | 9/1992 | Rose et al. . |
| 5,151,102 | 9/1992 | Kamiyama et al. . |
| 5,190,541 | 3/1993 | Abele et al. . |
| 5,201,900 | 4/1993 | Nardella . |
| 5,207,691 | 5/1993 | Nardella . |
| 5,217,458 | 6/1993 | Parins . |
| 5,258,006 | 11/1993 | Rydell et al. . |
| 5,269,780 | 12/1993 | Roos . |
| 5,277,201 | 1/1994 | Stern . |
| 5,281,216 | 1/1994 | Klicek . |
| 5,290,286 | 3/1994 | Parins . |
| 5,290,287 | 3/1994 | Boebel et al. . |
| 5,336,229 | 8/1994 | Noda . |
| 5,342,359 | 8/1994 | Rydell . |
| 5,395,369 | 3/1995 | McBrayer et al. . |
| 5,403,312 | 4/1995 | Yates et al. . |
| 5,439,464 | 8/1995 | Shapiro . |
| 5,443,463 | 8/1995 | Stern et al. . |
| 5,445,638 | 8/1995 | Rydell et al. . |
| 5,456,684 | 10/1995 | Schmidt et al. . |
| 5,458,598 | 10/1995 | Feinberg et al. . |
| 5,462,546 | 10/1995 | Rydell . |
| 5,486,155 | 1/1996 | Muller et al. . |
| 5,531,744 | 7/1996 | Nardella et al. . |
| 5,549,606 | 8/1996 | McBrayer et al. . |
| 5,558,671 | 9/1996 | Yates . |
| 5,573,534 | 11/1996 | Stone . |
| 5,599,350 | 2/1997 | Schulze et al. ............................ 606/50 |
| 5,688,270 | 11/1997 | Yates et al. . |
| 5,709,680 | 1/1998 | Yates et al. . |
| 5,810,811 | 9/1998 | Yates et al. . |
| 5,951,549 | 9/1999 | Richardson et al. ....................... 606/48 |

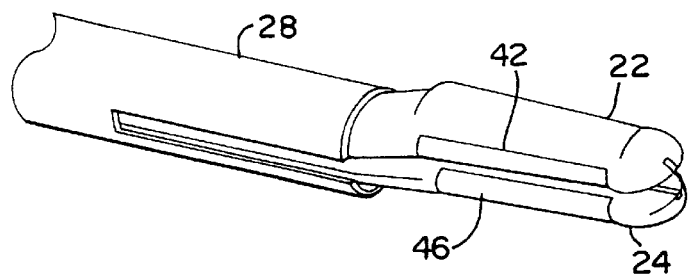
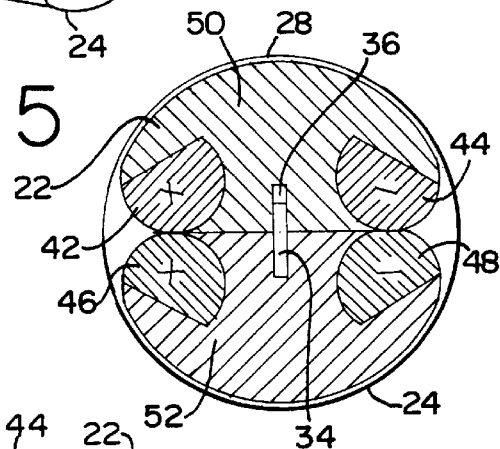
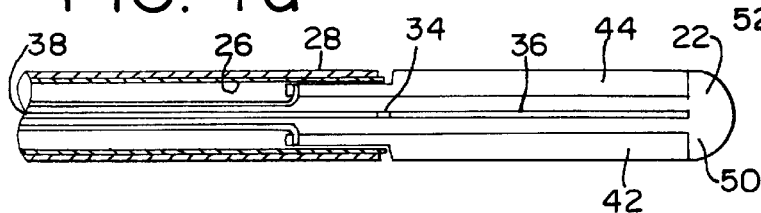
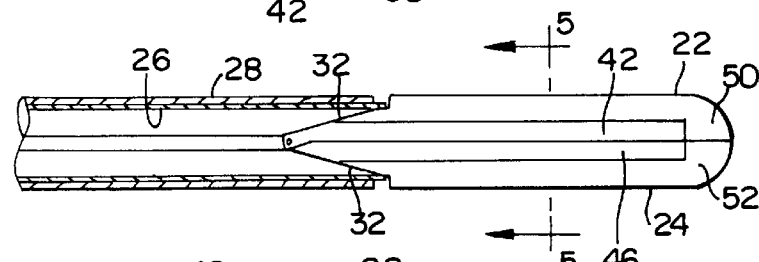
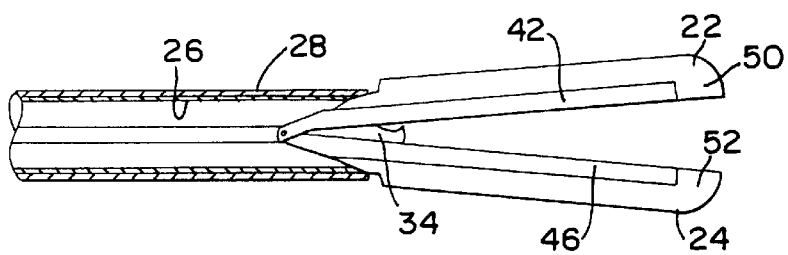
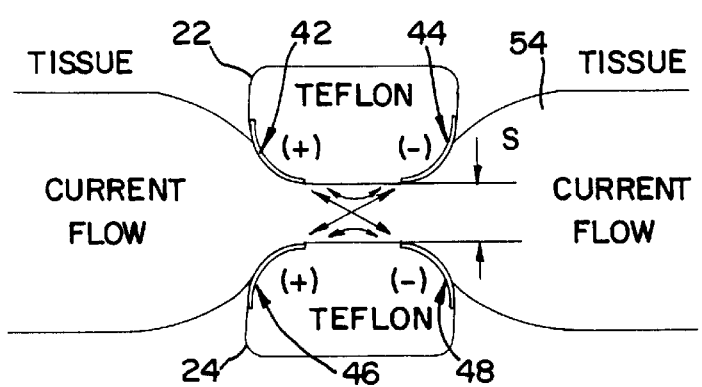

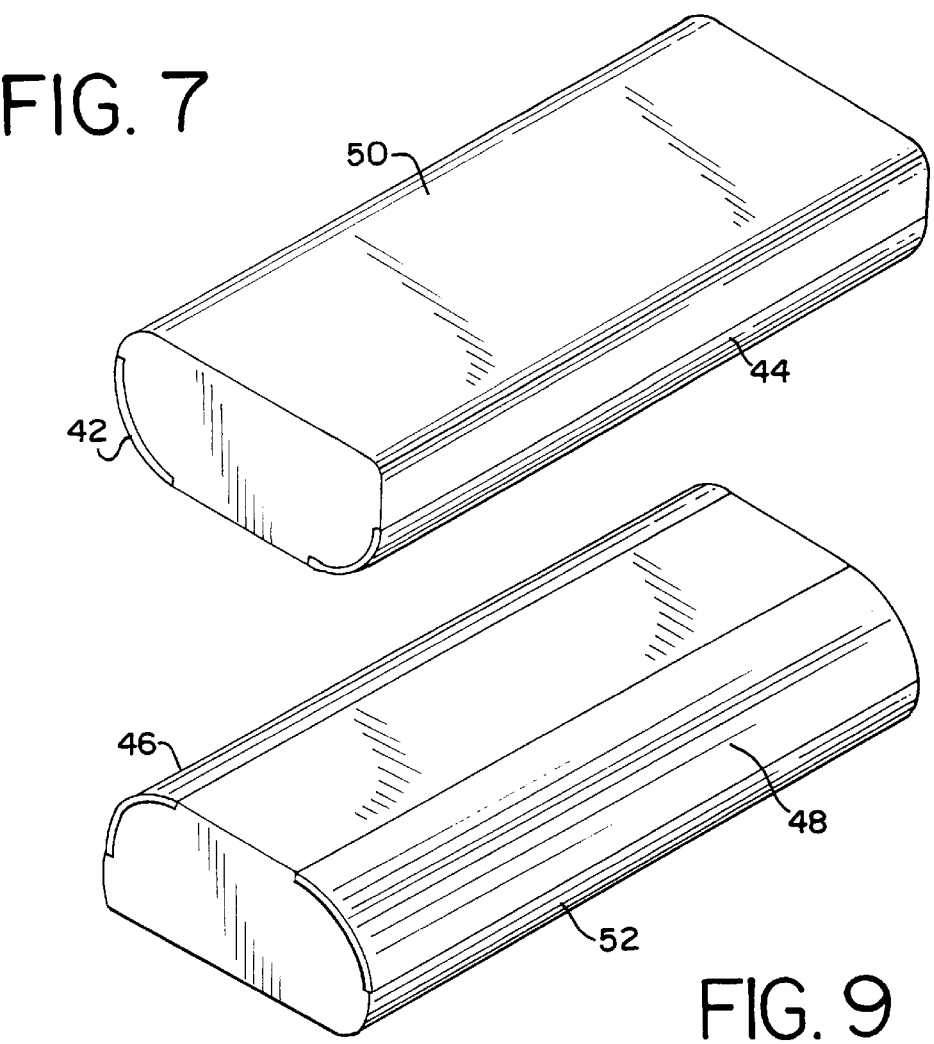
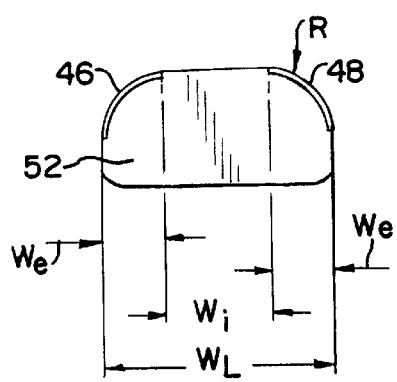
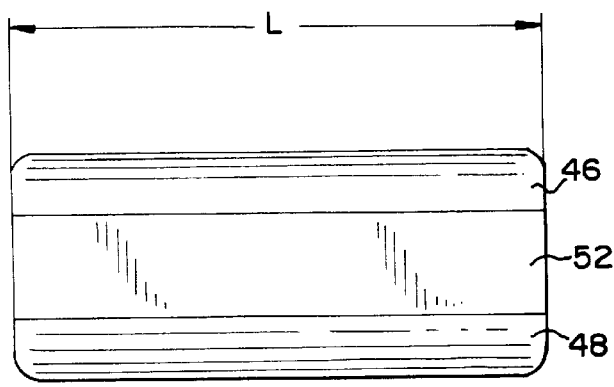

BIPOLAR TISSUE GRASPING APPARATUS AND TISSUE WELDING METHOD

The present invention relates to an electrosurgical instrument and, more particularly, to a bipolar electrosurgical grasper particularly useful for tissue welding.

BACKGROUND

The application of heat to treat bleeding wounds dates back to antiquity, with a hot iron being widely applied in medieval times to cauterize battle wounds to stop bleeding. In cauterization, the essential mechanism behind the treatment is using conductive heat transfer from a hot object to raise the temperature of the bleeding tissue sufficiently high to denature the tissue proteins.

Coagulation by means of electrosurgery is also accomplished by heating tissue, but the primary mechanism is electrical power dissipation in the affected tissue, rather than heat transfer from an external object. Current flows through the tissue, and is resisted by the tissue. This creates a small envelope of steam around the electrodes of the electrosurgical instrument, and the steam vaporizes the tissue to cause cellular dehydration, denaturation of proteins, and tissue shrinkage, leading to blood vessel thrombosis. This form of hemostasis is now routinely used in both open and endoscopic surgery for small blood vessels (typically smaller than 1 mm), and has largely replaced individual vessel ligation.

Currently-available bipolar grasping instruments for electro-coagulation of tissue, or "tissue welding," generally use only two electrodes of opposite polarity, one of which is located on each of the opposite jaws of the grasper. As illustrated in FIG. 1, in use, tissue is held between a pair of grasper jaws (shown in cross-section) having first and second electrodes (Electrode 1 and Electrode 2) of opposite polarity. Bipolar current flows between the two electrodes along the illustrated current flow lines, with tissue coagulating first at the edges of the jaws. Then, as the tissue dries out and the impedance increases, the current flows through the moister tissue and the coagulation spreads both inward toward the center of the jaws and outward from the jaw edges. The tissue coagulation and heating outside the jaw continues until the power is shut off.

Thermal damage to adjacent structures can occur due to this spread of thermal energy outside the jaws of the instrument. Because of the spread of thermal energy outside the jaws of the instrument, it is difficult to coagulate long sections of tissue, such as bowel, lung, or larger blood vessels, without significant lateral thermal spread. Over-coagulation frequently occurs, resulting in tissue sticking to the jaws of the instrument. When the jaws of the instrument are opened, if the tissue sticking is severe, the tissue can be pulled apart, thus adversely affecting hemostasis. Under-coagulation can occur if insufficient energy has been applied to the tissue, and the resulting hemostasis will be incomplete.

Thus, it is an object of the present invention to provide an electrosurgical tissue welding instrument in which the current pathway is limited to tissue within the jaws, so as to minimize tissue damage due to thermal effects outside the jaws of the device.

It is a further object of the present invention to provide an electrosurgical tissue welding instrument which allows coagulation of a relatively long section of tissue, while minimizing the lateral spread of thermal energy.

It is a still further object of the present invention to provide an electrosurgical tissue welding instrument in which the maximum current density in the coagulated tissue occurs away from the electrodes, and between two stick resistant surfaces, to minimize tissue sticking to the electrodes.

It is another object of the present invention to provide an electrosurgical tissue welding instrument where the current flow is self-limiting to prevent over-coagulation of the tissue.

It is an additional object of the present invention to provide an electrosurgical tissue welding instrument which provides a clear view of coagulated tissue to prevent under-coagulation of the tissue.

SUMMARY OF THE INVENTION

These objects, as well as others which will become apparent upon reference to the following detailed description and drawings, are accomplished by a bipolar electrosurgical instrument having a pair of relatively moveable jaws, each of which includes a tissue contacting surface. The tissue contacting surfaces of the jaws are in face-to-face relation with one another, and adjacent each of the tissue contacting surfaces are first and second spaced-apart electrodes that are adapted for connection to the opposite terminals of a bipolar RF generator so as to generate a current flow therebetween. The first and second electrodes of one jaw are in opposed relation, respectively, with the first and second electrodes of the other jaw. The tissue contacting surface is disposed between the electrodes on each jaw, and the first electrodes of each jaw are connectable to one terminal of the bipolar RF generator, while the second electrodes of each jaw are connectable to the other terminal of the bipolar RF generator.

The tissue contacting surface of each jaw member is substantially non-conductive, and preferably made of a stick-resistant material, such as polytetrafluoroethylene, polypropylene-polystyrene, polycarbonate or ABS, and is preferably transparent to facilitate visualization of the tissue coagulation. The electrodes on each jaw are disposed so that the maximum current density in the grasped tissue occurs away from the electrodes in the space between the two insulated surfaces of the tissue contacting surfaces.

Because each jaw is a bipolar electrode, multiple local current pathways, high current densities, and lower impediences are achieved. Indeed, the maximum current density is between the two insulated jaw surfaces, while a relatively lower current density exists at the electrode surfaces. Thus, the invention provides for self-limiting, controlled coagulation, as coagulation occurs initially at the center of the instrument and, as the impedance of the coagulated tissue increases, current flow to the electrodes decreases and automatically stops when coagulation is complete. Coagulation is limited to the area of the tissue held between the tissue contacting surfaces because there is no current flow between the opposed electrodes, which are of like polarity. Additionally, there is less sticking of the coagulated tissue to the grasper jaws because the coagulation occurs between the non-conductive stick resistant surfaces of the tissue contacting surfaces. Further, this design should work with most known electrosurgical generators, and have a greater coagulation efficiency than existing devices.

BRIEF DESCRIPTION OF THE DRAWINGS

FIG. 3. is an enlarged perspective view of the distal end of the endoscopic bipolar tissue grasper of FIG. 2, showing the jaw members in greater detail.

FIGS. 4a–c are top (FIG. 4a) and side (FIGS. 4b and c) views of the distal end of the graspers shown in FIG. 3, in partial cross-section to show the actuation mechanism for moving the grasper jaws between the closed (FIG. 4b) and open (FIG. 4c) positions.

FIG. 5 is a cross-sectional view of the grasper jaws taken along line 5—5 of FIG. 4b.

FIG. 6 is a cross-sectional view of the jaws of the inventive bipolar tissue graspers, with uncoagulated tissue disposed therebetween, showing the path of current flow between the two jaw members.

FIG. 7. is a perspective view of two disposable cartridge members that form the jaws of one embodiment of the present invention.

FIGS. 8 and 9 are, respectively, plan and end views of one of the cartridge members shown in FIG. 7.

DETAILED DESCRIPTION

Figure 2:
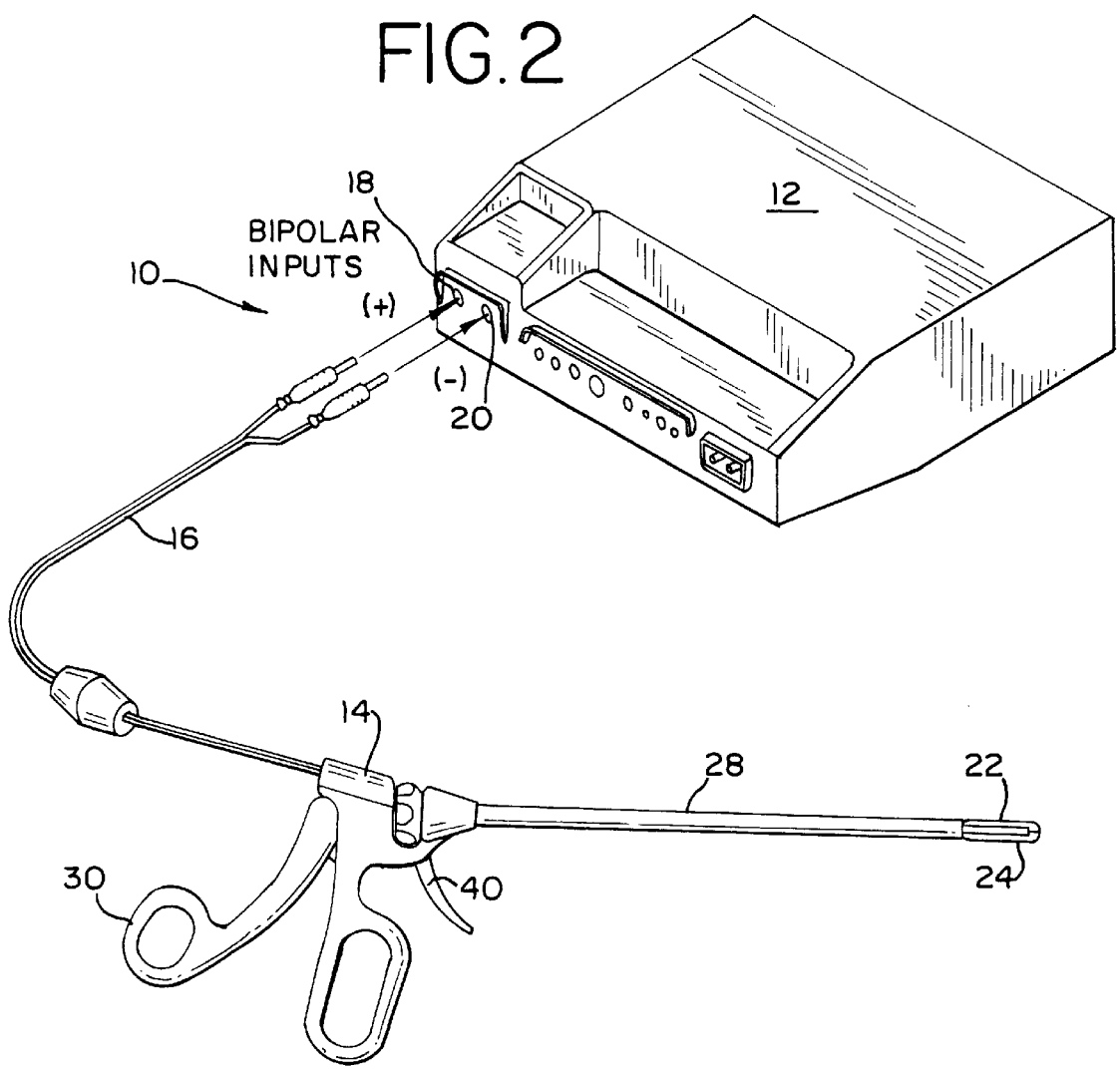
FIG. 2 is a perspective view of an endoscopic bipolar tissue grasper in accordance with the present invention shown with an associated electrosurgical current generating unit and connector table.

Turning to FIG. 2, there is seen a perspective view of an electrosurgical instrument system, generally designated 10, embodying the present invention. The illustrated system includes an RF energy generator 12, a hand-held, endoscopic electrosurgical graspers 14, and a cable 16 that connects the graspers 14 to the plug clip receptacles 18, 20 for positive and negative bipolar outputs of the generator 12. While the illustrated graspers 14 are endoscopic graspers for use in minimally invasive surgical procedures, the invention of the present application is equally applicable to graspers designed for use in open surgical procedures.

The illustrated RF generator 12 may be, for example, a unitary monopolar-bipolar RF generator, such as the Valley Lab Force 2 RF generator, and thus also include plug clip receptacles for the monopolar active and return terminals. However, for the purposes of the present invention, only the bipolar current generating feature is utilized.

The graspers 14 have two relatively moveable opposed jaws 22, 24, best seen in FIG. 3. The general construction and mechanism for actuation of the graspers 14 is well known in the art, and is typified by those graspers disclosed in U.S. Pat. Nos. 5,342,359 and 5,403,312, which are herein incorporated by reference. In general, a closure tube 26 is coaxially advanced through a sheath 28 by a trigger mechanism so as to engage a camming surface 32 on the jaws 22, 24 to close the jaws. Retraction of the closure tube moves the jaws to the open position (FIG. 4c).

The illustrated graspers also include a linear cutting element or knife 34 (best seen in FIGS. 4c and 5). As is well known, the knife 34 is advanced into a slot 36 in the jaws 22, 24 to cut tissue held between after the tissue has been coagulated. Again, the mechanism for advancing the knife is well known, and may include drive rod 38 that is advanced upon actuation of a trigger 40. While the illustrated graspers include a knife blade, the invention is equally applicable to simple graspers not including a cutting element.

In keeping with the present invention, each jaw includes a tissue contacting surface made of insulating material with two electrode surfaces carried adjacent the tissue contacting portions of each jaw. The tissue contacting surfaces of the jaws are in a generally face-to-face relationship, with the two electrodes associated with each jaw being spaced apart and in face-to-face relationship with the corresponding electrodes on the opposite jaw so that the electrodes in each face-to-face electrode pair is of a like polarity. This configuration for the electrodes, with the opposed electrodes in each face-to-face pair of electrodes being of the same polarity which is opposite to the polarity of the other face-to-face pair of electrodes, is similar to that shown in U.S. Pat. No. 2,031,682 to Wappler et al. (See FIG. 18).

Turning to FIGS. 3–5, the jaws 22, 24 include electrode pairs 42, 44 and 46, 48 respectively. The electrodes 42, 44 and 46, 48 are carried by the jaws 22, 24 adjacent the insulating members 50, 52, respectively. The insulating members form a tissue contacting surface on each jaw 22, 24 which is defined substantially by the surface on the insulating members 50, 52 that lies between their associated electrode pairs. However, the electrodes 42, 44 and 46, 48 also partially contact tissue grasped between the jaws.

As best seen in FIG. 5, the tissue contacting surfaces of each jaw are in face-to-face relationship, and the electrodes are connected to the terminals of a bipolar RF generator so that the electrodes of each face-to-face pair are of the same polarity, and one face-to-face electrode pair is the opposite polarity of the other face-to-face electrode pair. Thus, as illustrated in FIG. 5, face-to-face electrodes 42 and 46 are of a positive polarity, while face-to-face electrodes 44 and 48 are of a negative polarity.

Figure 1:
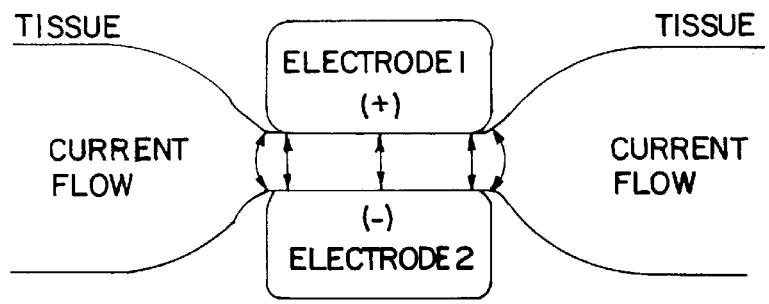
FIG. 1 is a cross sectional view of the jaws of the prior art bipolar graspers, with uncoagulated tissue disposed therebetween, showing the path of current flow between the two jaw members.

As shown in FIG. 6, this configuration of insulating members and electrodes provides for a current flow (as shown by the double dash headed arrows) through the tissue 54 between the electrodes of opposite polarity. There is no current flow through the tissue that is not held between the grasper jaws, and the current flow is at its maximum density between the tissue contacting surfaces of the jaws. Accordingly, tissue is coagulated first along the center of the jaws and, as the impedance of the tissue increases due to its coagulation, the current flow between the electrodes is cut-off. Thus, the flow of current between the electrodes naturally stops when coagulation is complete. This is in marked contrast to the prior art bipolar graspers illustrated in FIG. 1, in which current flow continues through the tissue held outside of the jaws until such time as the operator deactivates the electrodes.

Preferably, the insulating members 52, 54 comprising the tissue contacting surfaces are made of a non-stick, non-conductive material such as polytetreflouroethylene, polypropylene-polystyrene, polycarbonate or ABS. A substantially clear or transparent stick resistant insulating material permits the tissue held between the jaws to be viewed through the top or bottom surfaces of the jaw, thus allowing the operator to view the extent of tissue coagulation.

The electrodes 42, 44, 46, 48 are preferably are made of a conductive material such as aluminum, stainless steel, or gold. For better structural support, the electrodes themselves could be structural elements (as shown in FIGS. 3–5). Alternatively, the electrodes can be conductive strips adhered to the insulating members (as shown in FIGS. 7–9).

With reference to FIGS. 7–9, the electrodes 42, 44, 46, 48 may be made of, e.g., 0.003 inch aluminum tape adhered to Teflon polytetreflouroethylene insulating members 50, 52. In one embodiment the insulating members are 10 mm wide ($W_L$ in FIG. 9) and 40 mm long (L in FIG. 8), with the electrodes spaced 3 mm apart ($W_i$ in FIG. 9). It is contemplated that such a graspers construction will permit use of RF generator outputs of between 20 and 50 watts. In practice, insulating member widths ($W_L$) of 5 mm to 10 mm, electrode widths ($W_e$) of 1 mm to 4 mm, electrodes spacings ($W_t$) of 1 mm to 6 mm, and clamped jaw spacing (S in FIG. 6) of 1 mm–3 mm have produced excellent results. Insulating member lengths (L) from 10 mm to 50 mm have also produced excellent results.

Preferably, the graspers are constructed so that the clamped jaw spacing S is small enough relative to the electrode width to achieve a significantly higher current density in the tissue between the insulated surfaces than the current density through the tissue that contacts the electrode surfaces. This insures that current density at the electrodes is significantly less than the current density in the tissue held between the tissue contacting surfaces. Consequently, the tissue in contact with the electrodes will be coagulated less than the tissue held between the tissue contacting surfaces, and the tissue will be less likely to stick to the electrodes.

While the invention has been described in terms of certain preferred embodiments, there is no intent to limit the invention to the same. Indeed, it is intended to cover all apparatus and methods and their equivalents within the scope of the following claims. For example, in the embodiment of FIG. 5, the electrode pairs are structural members that also support the tissue contacting surfaces therebetween, while in the embodiment of FIGS. 6–9, the tissue contacting surfaces are structural members that each support a pair of electrodes. However, it is not necessary for either the electrodes or the tissue contacting surfaces to also comprise the structural members of the jaws. The jaws could comprise separate structural elements that support both the electrodes and the tissue contacting surfaces.

What is claimed is:

1. Tissue grasping apparatus comprising:
   first and second elongated grasping jaws, each jaw including a tissue contacting surface in face-to-face relation with the tissue contacting surface of the other jaw;
   said grasping jaws being relatively movable for grasping tissue between said tissue contacting surfaces;
   the tissue contacting surfaces of said jaws comprising an insulating material;
   at least two electrode surfaces carried adjacent said tissue contacting surfaces of each said jaw and disposed to engage said tissue when grasped, the two electrode surfaces on said first law being in face-to-face relation with the two electrode surfaces on said second jaw, and the facing electrode surfaces being of like polarity, said electrode surfaces being connectable to a power source for providing an electrical current between said electrode surfaces;
   whereby, when tissue is grasped between said tissue contacting surfaces electrical current may be caused to flow between said electrode surfaces and through the tissue grasped between said tissue contacting surfaces.

2. The apparatus of claim 1 in which the tissue contacting surface comprises a material selected from the group consisting of polytetraflouroethylene, polypropylene-polystyrene, polycarbonate, or ABS.

3. The apparatus of claim 1 in which the insulating material of the tissue contacting surface comprises a transparent material.

4. The tissue grasping apparatus of claim 1 wherein the density of the electrical current through the tissue is greater in the tissue disposed between the insulating material on said jaws than in the tissue contacting the electrode surfaces.

5. The apparatus of claim 1 wherein the tissue contacting surfaces of said first and second jaws each have opposed elongated edges and said electrode surfaces are located on the edges of the tissue contacting surfaces.

6. The apparatus of claim 1 wherein the insulating material comprises a non-stick material.

7. The apparatus of claim 1 wherein the electrode surfaces comprise a material selected from the group consisting of aluminum, stainless steel, or gold.

8. Tissue grasping apparatus comprising:
   two grasping jaws, each jaw including an insulating tissue contacting surface;
   said grasping jaws being relatively movable for grasping tissue between said tissue contacting surfaces;
   said jaws further comprising two spaced-apart electrode surfaces adjacent said insulating tissue contacting surface, said jaws being in generally face-to-face relationship to provide a first face-to-face electrode surface pair, face-to-face insulating surfaces, and a second face-to-face electrode surface pair;
   said electrode surfaces being connectable to a power source for providing an electrical current between said one and said other electrode surface pairs, the electrode surfaces comprising a particular face-to-face electrode surface pair being of like polarity; and
   whereby, when tissue is grasped between said tissue contacting surfaces electrical current may be caused to flow between said one and other electrode surface pairs and through the tissue grasped between said insulating surfaces.

9. The apparatus of claim 8 wherein the insulating surface of each tissue contacting surface comprises a non-stick material.

10. The apparatus of claim 9 wherein the non-stick material is selected from the group consisting of polytetraflouroethylene, polypropylene-polystyrene, polycarbonate, or ABS.

11. The apparatus of claim 8 wherein the insulating surface of each tissue contacting surface comprises a transparent material.

12. The tissue grasping apparatus of claim 8 wherein the density of the electrical current through the tissue is greater in the tissue disposed between the insulating material on said jaws than in the tissue contacting said face-to-face electrode surfaces.

13. The apparatus of claim 8 wherein the electrodes surfaces comprise a material selected from the group consisting of aluminum, stainless steel, or gold.

14. A method of promoting coagulation in tissue, comprising:
   providing a pair of grasping jaws, each jaw including an insulating tissue contacting surface in face-to-face relation with the tissue contacting surface of the other jaw, said jaws further comprising two spaced-apart electrode surfaces adjacent said insulating tissue contacting surface, said jaws providing first face-to-face electrode surface pair, face-to-face insulating surfaces, and a second face-to-face electrode surface pair, said electrode surfaces being connectable to a power source for providing an electrical current between said first and said second electrode surface pairs, the electrode surfaces comprising a particular electrode surface pair being of like polarity;
   closing said jaws on tissue to be coagulated, with said tissue contacting surfaces in contact with said tissue;
   connecting said electrode surfaces to a current source to create a current flow between said first and said second electrode surface pairs and through tissue located between said tissue contacting surfaces to promote coagulation of tissue grasped between said tissue contacting surfaces.

15. The method of claim 14 wherein the insulating surface of each tissue contacting surface comprises a non-stick material.

16. The method of claim 15 wherein the non-stick material is selected from the group consisting of polytetraflouroethylene, polypropylene-polystyrene, polycarbonate, or ABS.

17. The method of claim 14 wherein in insulating surface of each tissue contacting surface comprises a transparent material.

18. The method of claim 14 wherein the tissue to be coagulated is grasped between the insulating surfaces of said jaws.

19. Bipolar electrosurgical apparatus comprising a pair of jaws that are relatively movable toward and away from one another, each of said jaws including a non-conductive tissue contacting surface, said tissue contacting surfaces of said jaws being face-to-face relation with one another for contacting tissue located between said jaws as they move toward one another, each of said jaws including:
first and second spaced apart electrodes adjacent each of said tissue contacting surfaces for connection to different terminals of an RF generator to generate electrical current flow therebetween, said first and second electrodes of one jaw being in opposed relation, respectively, with first and second electrodes of the other jaw; and
said first electrodes of each jaw being connectable to one terminal of an RF generator and said second electrodes of each jaw being connectable to another terminal of an RF generator.

20. The bipolar electrosurgical apparatus of claim 19 in which said tissue contacting surface of each jaw is stick resistant.

21. The bipolar electrosurgical apparatus of claim 19 in which said tissue contacting surface of each jaw comprises a transparent material.

22. The bipolar electrosurgical apparatus of claim 19 in which said tissue contacting surface of each jaw comprises a material selected from the group consisting of polytetraflouroethylene, polypropylene-polystyrene, polycarbonate, or ABS.

23. The bipolar electrosurgical apparatus of claim 19 wherein the density of electrical current flow through tissue grasped between said jaws is greater in the tissue disposed between said spaced electrodes than in the tissue disposed between said opposed electrodes.

24. The apparatus of claim 19 wherein the electrodes comprise a material selected from the group consisting of aluminum, stainless steel, or gold.

25. A bipolar electrosurgical apparatus comprising a pair of facing jaws that are relatively movable toward and away from one another:

each of said jaws including a generally flat stick-resistant tissue contacting surface having a length defined by proximal and distal ends and a width defined by sides, said tissue contacting surface of each of said jaws being substantially identical in shape and in opposed relation to one another for contacting tissue located between said jaws as the jaws move toward one another;

first and second electrodes for connection to different terminals of an RF generator to generate electrical current flow therebetween;

one of said first and second electrodes being located on one or the other of said jaws on one side of said tissue contacting surface and the other of said electrodes being located on one or the other of said jaws on the other side of said tissue contacting surface; and whereby current flowing between said electrodes flows through tissue located between said tissue contacting surfaces.

26. The bipolar electrosurgical apparatus of claim 25 in which said tissue contacting surface comprises a material selected from the group consisting of polytetrafluoroethylene, polypropylene-polystyrene, polycarbonate, or ABS.

27. The bipolar electrosurgical apparatus of claim 25 in which said tissue contacting surface comprises a transparent material.

28. The bipolar electrosurgical apparatus of claim 25 wherein the density of electrical current flow through the tissue grasped between said jaws is greater in the tissue disposed between said opposed tissue contacting surfaces than in the tissue in contact with said first electrodes or said second electrodes on said jaws.

29. The apparatus of claim 28 wherein the electrodes comprise a material selected from the group consisting of aluminum, stainless steel, or gold.

\* \* \* \* \*